(12) United States Patent
Levy et al.

(10) Patent No.: US 9,463,099 B2
(45) Date of Patent: Oct. 11, 2016

(54) ORTHOPEDIC EXPANDABLE DEVICES

(71) Applicants: Mark M Levy, Raanana (IL); Eran Ishay, Tel Aviv (IL); Jaffar Hleihil, Jish (IL); Shimon Spector, Matan (IL); Nimrod Meller, Kfar Yehoshua (IL)

(72) Inventors: Mark M Levy, Raanana (IL); Eran Ishay, Tel Aviv (IL); Jaffar Hleihil, Jish (IL); Shimon Spector, Matan (IL); Nimrod Meller, Kfar Yehoshua (IL)

(73) Assignee: Expanding Orthopedics Inc., Memphis, TN (US)

( * ) Notice: Subject to any disclaimer, the term of this patent is extended or adjusted under 35 U.S.C. 154(b) by 62 days.

(21) Appl. No.: 14/210,473

(22) Filed: Mar. 14, 2014

(65) Prior Publication Data

US 2015/0257894 A1    Sep. 17, 2015

(51) Int. Cl.
*A61F 2/44* (2006.01)
*A61F 2/46* (2006.01)
*A61F 2/28* (2006.01)
*A61F 2/30* (2006.01)

(52) U.S. Cl.
CPC .............. *A61F 2/447* (2013.01); *A61F 2/442* (2013.01); *A61F 2/4611* (2013.01); *A61F 2002/2835* (2013.01); *A61F 2002/30019* (2013.01); *A61F 2002/30062* (2013.01); *A61F 2002/30092* (2013.01); *A61F 2002/30365* (2013.01); *A61F 2002/30367* (2013.01); *A61F 2002/30464* (2013.01); *A61F 2002/30471* (2013.01); *A61F 2002/30484* (2013.01); *A61F 2002/30515* (2013.01); *A61F 2002/30522* (2013.01); *A61F 2002/30523* (2013.01); *A61F 2002/30538* (2013.01); *A61F 2002/30548* (2013.01); *A61F 2002/30556* (2013.01); *A61F 2002/30579* (2013.01); *A61F 2002/30581* (2013.01); *A61F 2002/30584* (2013.01); *A61F 2002/30624* (2013.01); *A61F 2002/30626* (2013.01); *A61F 2002/30828* (2013.01); *A61F 2002/30831* (2013.01); *A61F 2002/448* (2013.01); *A61F 2002/4415* (2013.01); *A61F 2002/4475* (2013.01); *A61F 2310/00023* (2013.01); *A61F 2310/00359* (2013.01)

(58) Field of Classification Search
CPC .... A61F 2/4455; A61F 2/446; A61F 2/4465; A61F 2/447; A61F 2002/4415; A61F 2002/448; A61B 17/025; A61B 17/0256; A61B 17/0268
See application file for complete search history.

(56) References Cited

U.S. PATENT DOCUMENTS

| | | | |
|---|---|---|---|
| 6,176,882 B1 * | 1/2001 | Biedermann et al. ..... | 623/17.15 |
| 7,217,293 B2 * | 5/2007 | Branch, Jr. ........... | A61F 2/4611 |
| | | | 623/17.11 |
| 7,708,779 B2 * | 5/2010 | Edie et al. ................. | 623/17.15 |
| 2007/0255415 A1 * | 11/2007 | Edie et al. ................. | 623/17.16 |
| 2007/0260314 A1 * | 11/2007 | Biyani ........................ | 623/17.11 |
| 2008/0125865 A1 * | 5/2008 | Abdelgany ............... | 623/17.16 |
| 2008/0140207 A1 * | 6/2008 | Olmos .................. | A61F 2/4455 |
| | | | 623/17.16 |
| 2008/0147193 A1 * | 6/2008 | Matthis et al. ............ | 623/17.16 |
| 2011/0009969 A1 * | 1/2011 | Puno ......................... | 623/17.12 |
| 2011/0130835 A1 * | 6/2011 | Ashley et al. ............. | 623/17.11 |
| 2011/0282453 A1 * | 11/2011 | Greenhalgh ....... | A61B 17/8858 |
| | | | 623/17.16 |
| 2012/0215316 A1 * | 8/2012 | Mohr et al. ............... | 623/17.16 |

(Continued)

*Primary Examiner* — Lynnsy Summitt
(74) *Attorney, Agent, or Firm* — Dekel Patent Ltd.; David Klein

(57) ABSTRACT

An expandable bone device that includes a plurality of linking elements pivotally connected to one another about a hinge, wherein each of the linking elements has upper and lower support plates. An expansion mechanism is operatively connected to the linking elements and can move the upper support plate closer or further with respect to the lower support plate.

9 Claims, 8 Drawing Sheets

(56) References Cited

U.S. PATENT DOCUMENTS

2013/0274884 A1* 10/2013 Matsumoto .............. A61F 2/44
　　　　　　　　　　　　　　　　　　　　　　　　　　623/17.16

2014/0094916 A1* 4/2014 Glerum ................. A61F 2/442
　　　　　　　　　　　　　　　　　　　　　　　　　　623/17.15

2014/0277499 A1* 9/2014 Ainsworth ............ A61B 17/70
　　　　　　　　　　　　　　　　　　　　　　　　　　623/17.16

* cited by examiner

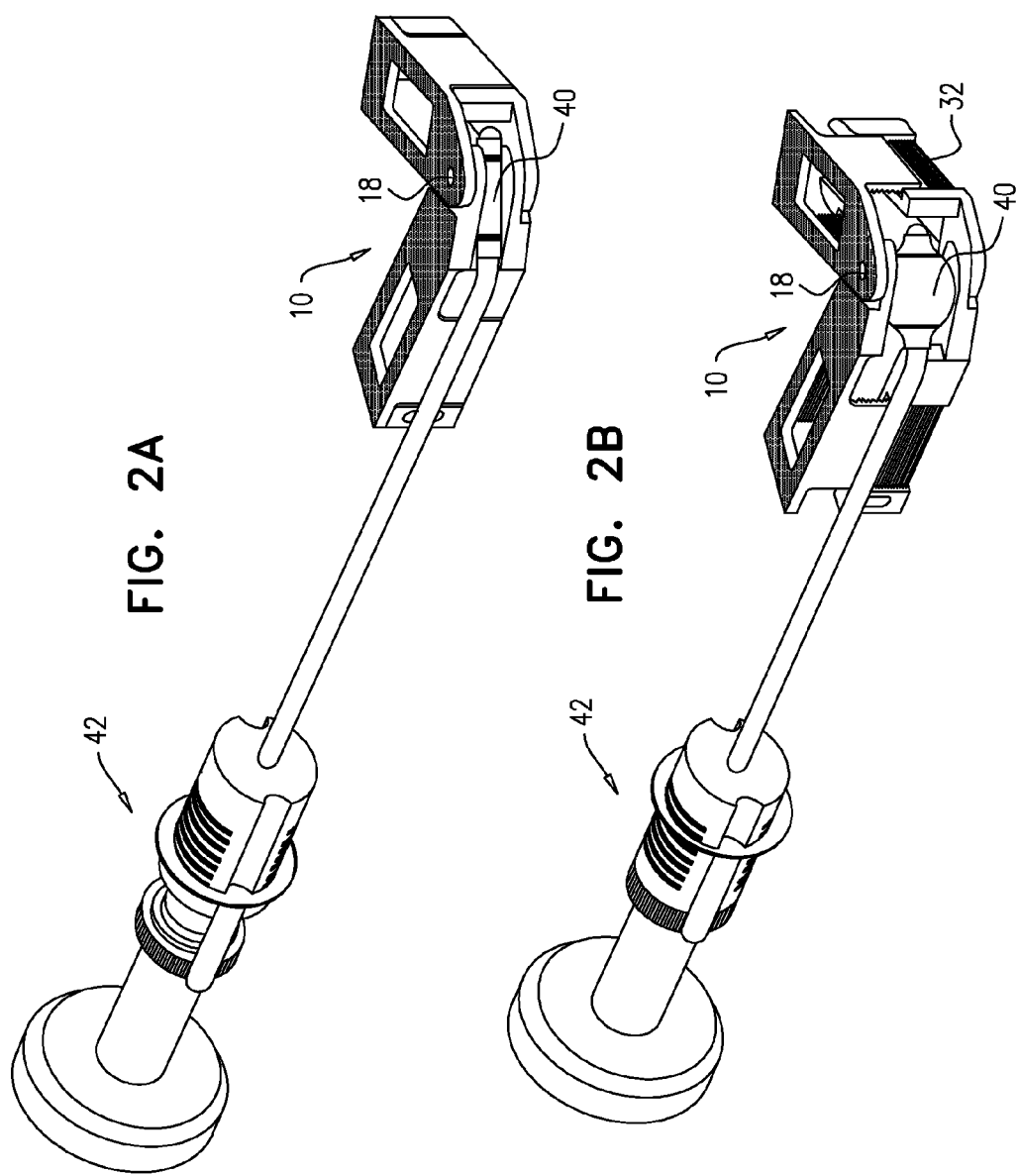

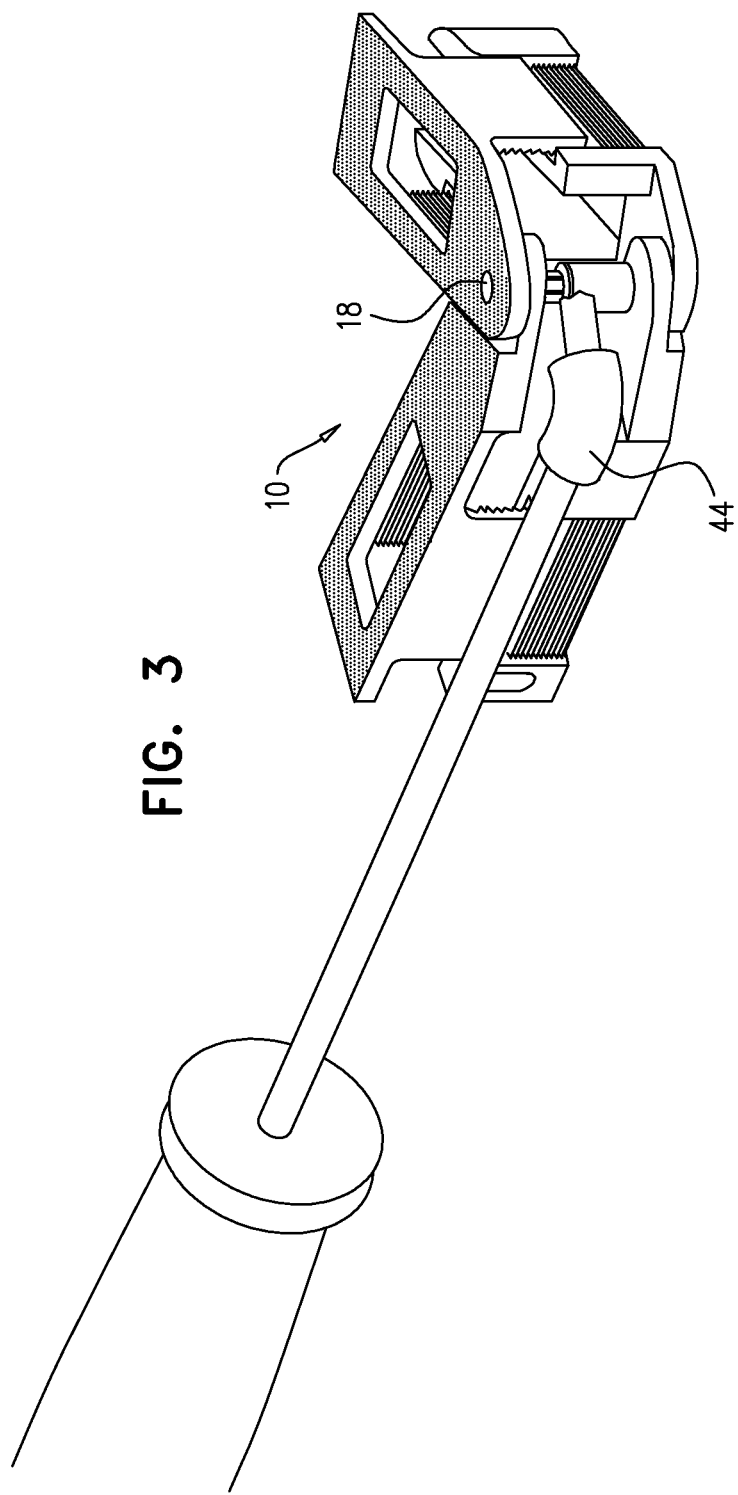

ORTHOPEDIC EXPANDABLE DEVICES

CROSS-REFERENCE TO OTHER APPLICATIONS

This application claims priority from U.S. Provisional Patent Application 61/786,655, filed Mar. 15, 2013.

FIELD OF THE INVENTION

The present invention relates generally to medical devices, and, more particularly, to implantable devices used to strengthen or support bony structures in the body, such as but not limited to, intervertebral or intravertebral devices to stabilize the human spine.

BACKGROUND OF THE INVENTION

Implant devices, such as vertebral spacers, intravertebral or intervertebral fusion devices and disc replacement devices, have been developed to assist with stabilization and fixation or functional support of the spine. Examples include pre-assembled rings, cages, boxes, dowels, and wedges of varying size and construction, such as meshes or plates, movable disc surfaces, gel or polymer spacers, elastomers and structures. However, all existing devices have certain drawbacks, such as difficulty of construction, insertion, bulkiness, inadequate surface coverage in area and/or height, multiple sizes (inventory) and others.

PCT/US2012/045495 to Levy et al. describes devices for use in the spine as an expandable cage for spine fusion and for intra-vertebral use for VCF (vertebral compression fracture) repair. Other embodiments see use as a disc replacement device, a dynamic application allowing movement. The devices include MIS (minimal invasive surgery)/cannulated (or not cannulated) devices delivered over a guide wire, with expandable capability for height control (to regain disc space height or vertebral body height). Some devices include units connected like a train, which are installed with a delivery system that can be manipulated for positioning and sequential deployment of one or more units or deployment of the train as a whole. The train-style units can be a closed structure, e.g., a sleeve or a tube in the shape of a closed ring, or an open structure.

SUMMARY OF THE INVENTION

The present invention seeks to provide novel implantable devices used to strengthen or support bony structures in the body, such as but not limited to, intravertebral or intervertebral fusion devices, as is described more in detail further below. The devices include features not found in the devices of PCT/US2012/045495, and can be used in similar procedures as those devices.

In one embodiment of the invention, the device can be installed through just one side of the vertebra (or in the disc space) in a minimal invasive way (but delivery at both sides is also possible). Materials include, without limitation, hard or soft, non-resorbable, resorbable, natural or synthetic, biological, mixed, including metal, polymers, bone (allograft or other), PEEK (polyetheretherketone), PEKK (polyetherketoneketone), PEK (polyetherketone), cells, tissue culture products, PET (polyethylene terephthalate), nylon, DACRON, KEVLAR, PE (polyethylene), PTFE (polytetrafluoroethylene), polyester, memory alloys or polymers, PMMA (poly(methyl methacrylate)), etc., or combinations thereof.

In another embodiment the structure can be installed though one side and left open but located near the cortical wall of the broken bone, to rebuild the lost original vertebra structure, as in the anterior and lateral walls of the vertebral body in a compression fracture with an anterior wedge shape. Any of those embodiments may include additional ways or attachments to further connect the device to the bone (other than surface contact), allowing a stand-alone static or a dynamic function, depending on the desired application.

The devices of the invention have other uses in bones in other parts of the skeleton besides the spine. For example, the device can be used as a bone spacer/filler in different bone locations, and can also be introduced in between bones or joint spaces when fusion or arthrodesis is attempted or for bone reconstruction proposes. As another example, in a dynamic application, the device can be used as a MIS (minimally invasive surgery) temporary or definitive total joint replacement device, partial joint replacement device, joint spacer or meniscus replacement device. The devices can be used with bone graft, biological bone cement, bone substitutes, gels, polymers, PMMA or combinations, etc. to enhance attachment to bone surface.

In one embodiment of the invention, the expandable bone device is positioned between two vertebrae, serving as a substitute for an intervertebral disc, such as in a fusion procedure. The expandable bone device acts as a spacer that enhances the fusion construction stability and promotes anterior bone column continuity when fusion occurs. The device is introduced through a small portal of entry (minimally invasive), which reduces surgical trauma and minimizes the inventory needed to cover all sizes and levels. Once located, the device is expanded in height to an optimal fit in the disc space.

The expandable bone device includes two or more linking elements, which can be inserted in a straight or slightly angled alignment, and which are then adjusted to the contour of the anatomy (e.g., disc space) by passive, active or self-steering of the individual elements. The linking elements can be provided in different sizes (including both symmetric and asymmetric combinations of elements) to accommodate different anatomies (different sizes of discs, for example) and for higher or lower expansion of the linking elements. The devices of the invention may optionally be affixed with additional screws to the vertebral body (or other structure in the body) or a standalone device (e.g., without additional pedicle screws).

The linkage can be a hinge, an elastically or plastically deformed flexure, X-shaped scissors or linkage with symmetrical or non-symmetrical arms, or other types of connection between the elements. The degree of articulation of the elements provides dimensional adjustment in the horizontal plane of the element (including expansion, contraction and bending or curling). A mechanical block or stop is provided to lock the articulated configuration in place after the desired articulation has been achieved.

In one embodiment of the invention, apertures or windows are formed in the device, such as but not limited to, the top and bottom plates of the device, the side walls and the proximal and distal tips of the device. Bone graft or bone substitute materials can be packed inside the device through those windows prior to implantation, which eventually fuse with the vertebral bone. The windows at the proximal and distal tips of the device can be used if a guide wire is used for initial placement of the device in the disc space.

In one embodiment of the invention, the front face of the leading element (that is, the first element to enter the introduction site in the patient's body) has a tapered or chamfered nose to facilitate insertion of the device into the disc space or other body cavity. The last element of the device has a feature that allows attachment and passage of tools (e.g., insertion tools, expansion tools, etc.).

The invention provides different methods and structure for expansion of the interconnected elements. Non-limiting examples include a balloon or a jack (e.g., screw or scissors-type jack), a gear with one or more meshed gear wheels or pinions, an asymmetric turning bolt, an elastically deformed actuator (shape memory alloy, elastomeric or any material with a suitably high percentage of elongation), a plastically deformed actuator (acting as an expandable appliance), wedge element, hydraulic or pneumatic elements, timing belt, self-expanding elements (e.g., made of NITINOL) activated by body temperature, or any other mechanism that can be permanently attached to the elements or removable.

The expansion can be parallel, producing a uniform expansion in height between the superior and inferior aspects of the device. Alternatively, the expansion can be parallel but if the plates are made out of a different thickness, the end shape after expansion can produce a slight angle between the anterior and posterior aspects of the device after placement and expansion, mimicking the natural angulation of some of the intervertebral discs (e.g., L5-S1). Alternatively, the expansion can be non-parallel and/or non-symmetrical, such as by expanding only in a single point/area of the device, where the linkage is usually placed, thereby producing an expansion at a slight angle to the anterior posterior plane (as in L5-S1). Combinations of asymmetrical plates with asymmetrical expansion are also covered by the scope of this application. Another possible expansion is symmetrical at the pivot of two connecting linkages which are articulated at their center (creating an X shape between them).

Also in the case of a spine disc, the structure can be inserted through one side of the disc space and either or both of the upper and lower support plates may include additional attachment structure (such as, but not limited to, mounting holes, lugs or tabs, etc., for screws or other fasteners) for attachment to the superior and inferior vertebra as a stand-alone device, statically for fusion or dynamically to allow desired movement.

In one embodiment of the invention, the expandable bone device can be a positive, self-locking expandable bone device. For example, after expansion to the required height, the device can be locked in place by a ratchet mechanism. The ratchet structure may be attached to the walls of the elements, and produces a positive lock at the desired height. The ratchet structure provides small increments in height, which are easily controlled by the user.

In one embodiment of the invention, mechanical seizure may be avoided by enclosing the moving parts so they smoothly glide in a fixed niche case. Additionally or alternatively, one or more guides can be used to guide the movement of the parts and prevent seizure. If a ratchet is used with a guide, the inner free end of the guide or some other tool can be used to release the ratchet, e.g., by pushing the ratchet outwards or inwards, so as to disengage the ratchet and allow the device to collapse down to its initial position, or by elastically deforming the wall to which the ratchet is engaged, thereby freeing the ratchet from the wall. If a ratchet is used, a transverse beam may be added between free ends of the internal wall of the device to avoid collapse of the center of the device which could cause disengagement of the ratchet.

As another example, after expansion to the required height, the device can be locked in place by a fixed jack or by a combination of jack and ratchet mechanism. Combined jack-ratchet expansion mechanisms with symmetrical or non-symmetrical expansion are in the scope of this application.

BRIEF DESCRIPTION OF THE DRAWINGS

The present invention will be understood and appreciated more fully from the following detailed description, taken in conjunction with the drawings in which:

FIGS. 2A and 2B are simplified illustrations of another mechanism (balloon) for expanding the expandable bone device, in accordance with another embodiment of the invention;

FIG. 3 is a simplified illustration of another mechanism (jack) for expanding the expandable bone device, in accordance with another embodiment of the invention;

DETAILED DESCRIPTION OF EXEMPLARY EMBODIMENTS

Figure 1A:
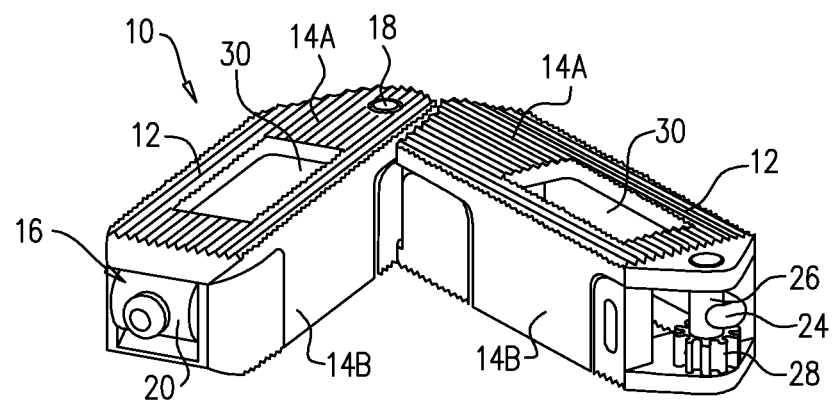
FIGS. 1A and 1B are simplified illustrations of an expandable bone device, constructed and operative in accordance with another embodiment of the present invention, in a contracted orientation.
Figure 1B:
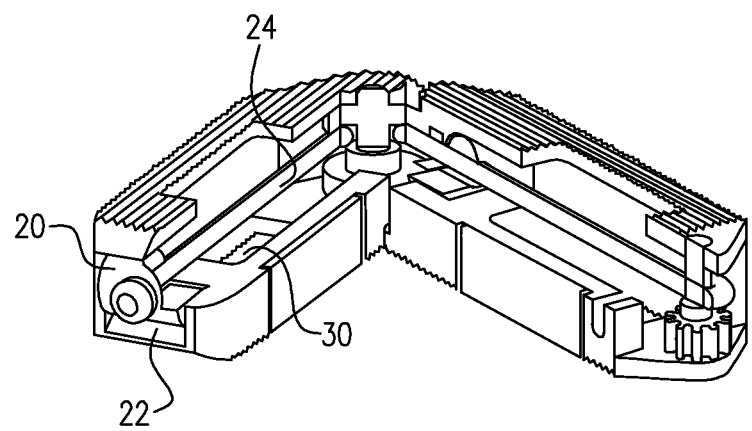
Figure 1C:
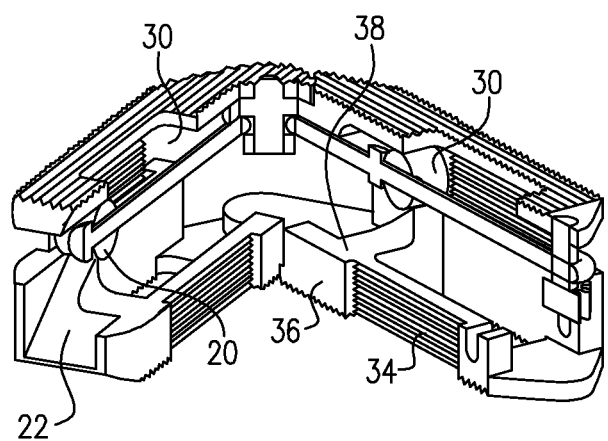
FIGS. 1C and 1D are simplified illustrations of the expandable bone device in an expanded orientation (using a wedge mechanism)
Figure 1D:
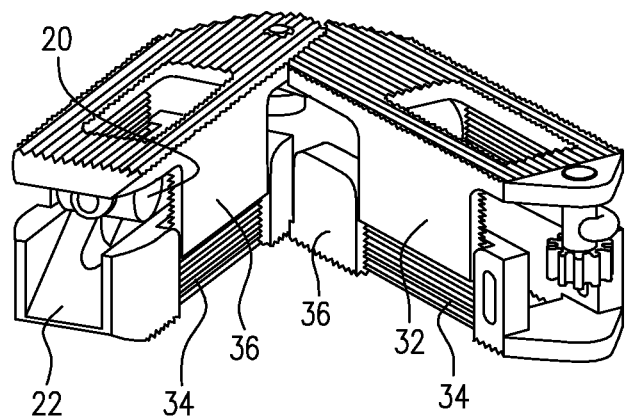

Reference is now made to FIGS. 1A-1D, which illustrate an expandable bone device 10, constructed and operative in accordance with an embodiment of the invention, in a contracted orientation (FIGS. 1A-1B) and an expanded orientation (FIGS. 1C and 1D).

Expandable bone device 10 includes a plurality of linking elements 12, each of which includes upper and lower support plates 14A and 14B, which in this embodiment, may be expanded by an intermediate wedge mechanism 16, as is described further below. Adjacent linking elements 12 are pivotally connected to one another with hinges 18.

In one embodiment, the wedging mechanism 16 includes a block 20 of any suitable size and shape, arranged to slide on a ramp 22 formed in one of the linking elements 12. Block 20 is connected to a wire or other slender element 24, which wraps around hinge 18 and is wound on an axle 26 of a gear drive 28. Gear drive 28 is rotatable by a suitable actuator (not shown), such as a gear motor. By suitable rotation of gear drive 28, slender element 24 is wound around axle 26 and pulls block 20 up ramp 22. This causes upper support plate 14A to be raised with respect to lower support plate 14B, as is seen in FIGS. 1C and 1D. Rotation of gear drive 28 in the opposite direction lowers upper support plate 14A towards lower support plate 14B.

Linking elements 12 can be inserted in a straight or slightly angled alignment, and then can be adjusted to the contour of the anatomy (e.g., disc space) by active or self-steering of the individual elements. Hinge 18 can be ratcheted to help maintain the angular orientation of the linking elements 12.

In one embodiment of the invention, apertures or windows 30 are formed in the device 10, such as but not limited to, in upper and lower support plates 14A and 14B, the side walls and the proximal and distal tips of the device. Bone graft or bone substitute materials can be packed inside the device through those windows prior to implantation, which eventually fuse with the vertebral bone.

In one embodiment of the invention, the proximal and distal faces of the pair of linking elements 12 are tapered, chamfered or rounded to facilitate insertion of the device into the disc space or other body cavity.

In one embodiment of the invention, expandable bone device 10 has a ratchet mechanism 32 for positive, self-locking of the device at a desired height. Ratchet mechanism 32 includes a pawl plate 34 that ratchets with teeth 34 formed on a side wall 36 of device 10 (FIG. 1D). Ratchet mechanism 32 provides small increments in height, which are easily controlled by the user. A transverse beam 38 (FIG. 1C) may extend between internal faces of side walls 36 to strengthen the structure and avoid collapse of the center of the device which could cause disengagement of the ratchet.

Figure 1E:
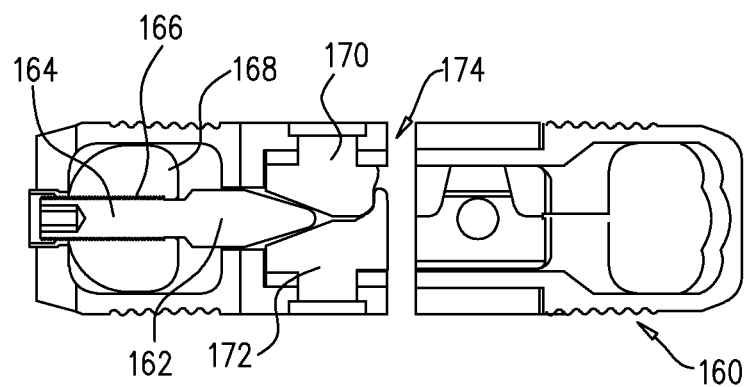
FIGS. 1E and 1F are simplified pictorial and sectional illustrations of an expandable bone device using another wedge mechanism, constructed and operative in accordance with an embodiment of the present invention.
Figure 1F:
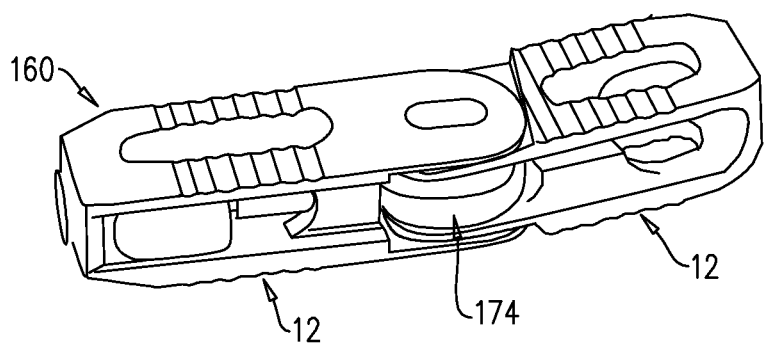

Reference is now made to FIGS. 1E and 1F, which illustrate an expandable bone device using another wedge mechanism 160. Wedge mechanism 160 includes a wedge head 162 on an end of a threaded shaft 164, which is threadedly received in a tapped bore 166 of a bushing 168. Wedge head 162 is wedged between upper and lower pivot members 170 and 172, respectively, of a joint 174 which pivotally connects linking elements 12. By screwing shaft 164 towards the pivot members, the wedge head 162 separates pivot members 170 and 172 from one another, which causes upper and lower support plates 14A and 14B to be distanced more from each other at the joint 174. The upper and lower support plates 14A and 14B are thus inclined, with the end at joint 174 higher than the end further away from joint 174.

Reference is now made to FIGS. 2A and 2B, which illustrate another mechanism for expanding the expandable bone device 10, in accordance with another embodiment of the invention. In this embodiment, a balloon 40 is placed at the hinge 18 and expanded with a fluid source 42 (pressurized saline or air, for example). Since expansion of balloon 40 occurs at the hinge 18, the ratchet mechanism 32 can have the ratcheting pawl and teeth at an angle so that the expansion can be non-parallel and/or non-symmetrical, thereby producing an expansion at a slight angle to the anterior posterior plane (as in L5-S1). Balloon 40 is an example of an expansion device which can be removed and even re-inserted, if desired.

Reference is now made to FIG. 3, which illustrates another mechanism for expanding the expandable bone device 10, in accordance with another embodiment of the invention. In this embodiment, a jack 44 is placed at or near hinge 18 and used to raise or lower upper support plate 14A with respect to lower support plate 14B. Jack 44 may be, without limitation, a mechanical jack (e.g., screw, scissors or others), or a hydraulic or pneumatic jack, or electrically operated jack.

Figure 4A:
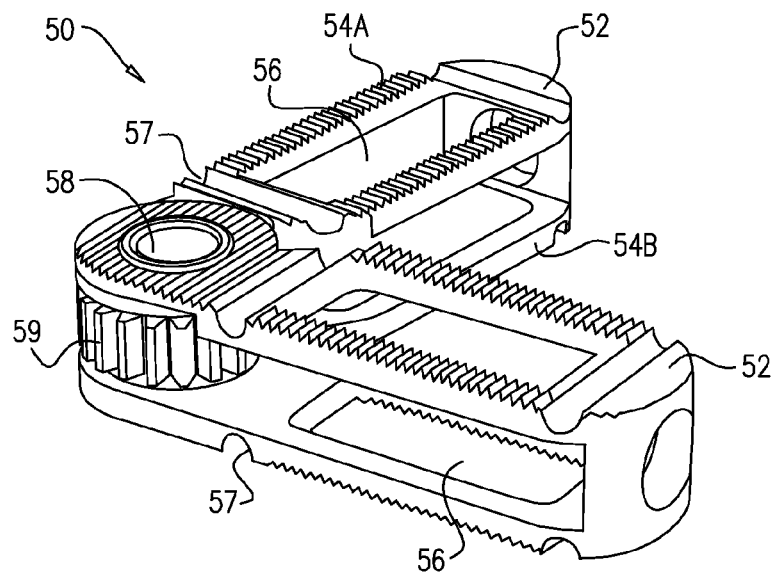
FIGS. 4A and 4B are simplified illustrations of expandable bone devices, constructed and operative in accordance with other embodiments of the present invention, in contracted orientations.

Reference is now made to FIG. 4A, which illustrates an expandable bone device 50, constructed and operative in accordance with an embodiment of the invention. Device 50 has a hinge 58 provided with a gear wheel 59, which may be ratcheted. Device 50 includes a plurality of linking elements 52, each of which includes upper and lower support plates 54A and 54B, which may be expanded by a wedge mechanism or jack or other means (not shown). Linking elements 52 are connected at a hinge 58 provided with a gear wheel 59, which may be ratcheted. Relatively large apertures 56 are formed in the device, such as but not limited to, the top and bottom plates of the device (upper and lower support plates 54A and 54B), the side walls and the proximal and distal tips of the device. Such large apertures can have additional sections to form parts of a wall.

The upper and lower support plates 54A and 54B may be formed with concave undercuts 57 so that upon expansion the plates bend along undercuts 57, thus providing asymmetric bending or expansion. This can be designed to meet the needs of a particular application.

Figure 4B:
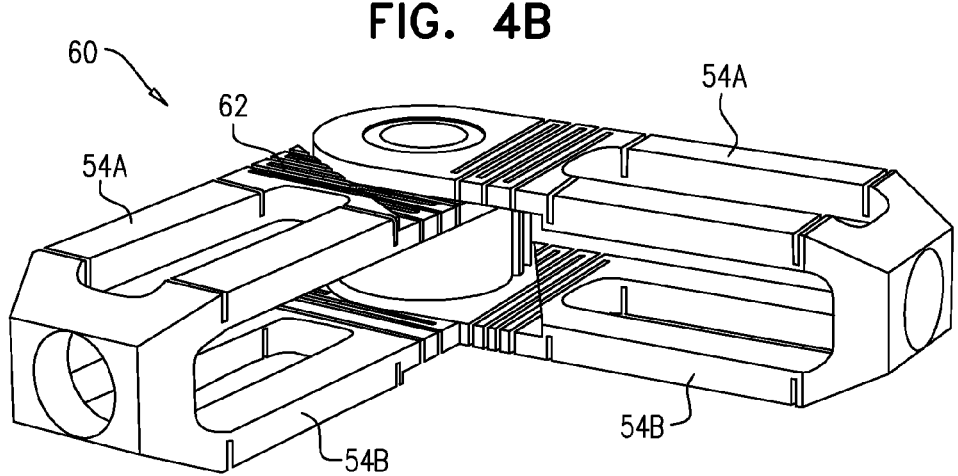

Reference is now made to FIG. 4B, which illustrates an expandable bone device 60, constructed and operative in accordance with an embodiment of the invention. Device 60 is similar to device 50, with like elements being designated by like numerals. Device 60 differs from device 50 in that device 60, instead of undercuts, has bend grooves 62 formed in one or more of upper and lower support plates 54A and 54B. Grooves 62 can provide asymmetric bending or expansion.

The invention provides different embodiments of force transmission mechanisms for transferring an expansion or turning force to the individual elements.

Figure 5A:
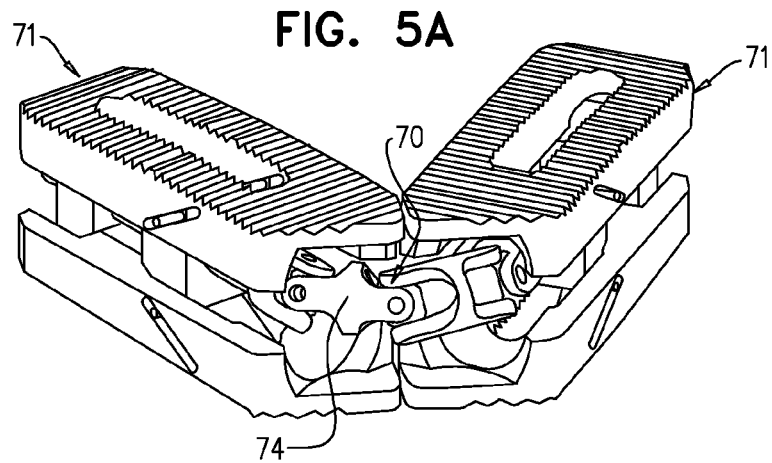
FIGS. 5A and 5B are simplified pictorial and exploded illustrations, respectively, of a force transmission mechanism that uses a universal joint mechanism, constructed and operative in accordance with an embodiment of the invention.
Figure 5B:
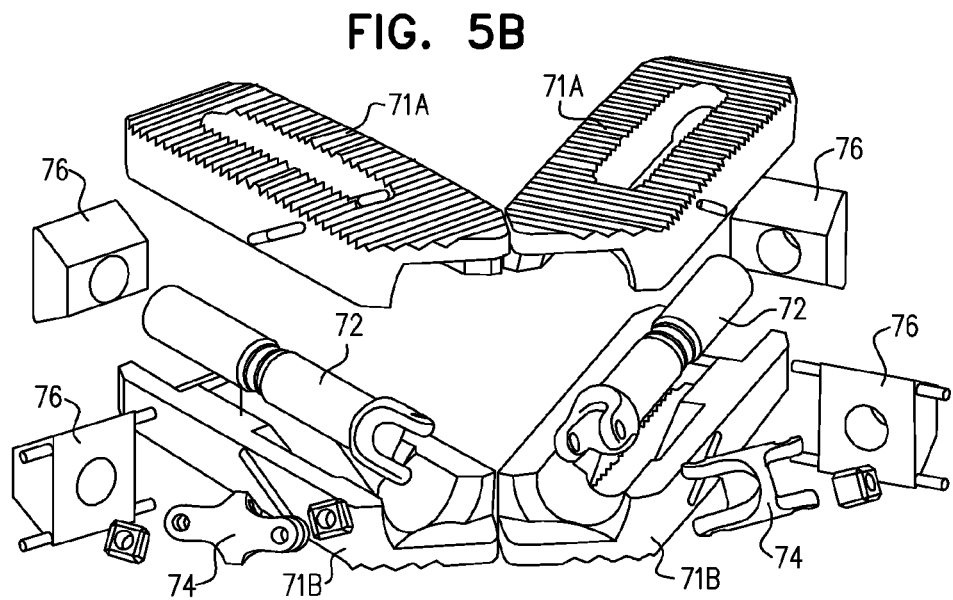

Reference is now made to FIGS. 5A and 5B, which illustrate a force transmission mechanism 70, constructed and operative in accordance with an embodiment of the invention. Force transmission mechanism 70 can be used in conjunction with any of the wedge or jack expansion mechanisms of the invention.

Figure 5C:
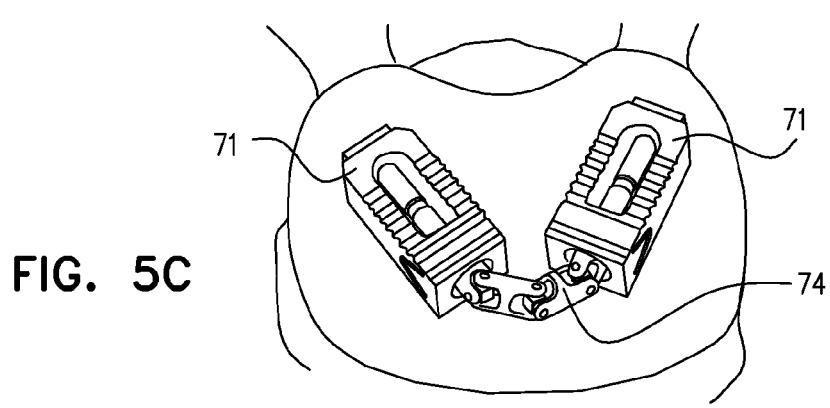
FIG. 5C is a simplified illustration of linking elements of FIGS. 5A and 5B in a disc space.

Force transmission mechanism 70 includes a torque shaft 72 that passes through linking elements 71. Each linking element 71 has upper and lower plates 71A and 71B. Adjacent torque shafts 72 are connected by a universal joint mechanism 74 (also referred to as a cardan). The torque shafts 72 are journaled in bearing supports 76. FIG. 5C illustrates the linking elements 71 in a disc space.

Figure 6A:
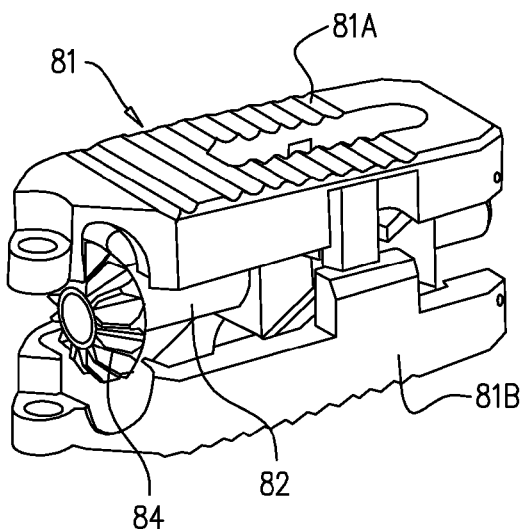
FIGS. 6A, 6B and 6C are simplified illustrations of a force transmission mechanism which uses a worm gear mechanism, constructed and operative in accordance with another embodiment of the invention.
Figure 6B:
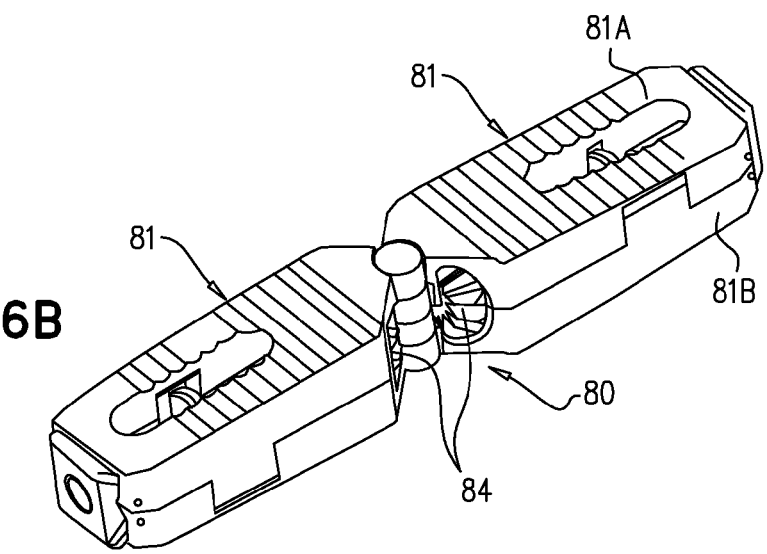
Figure 6C:
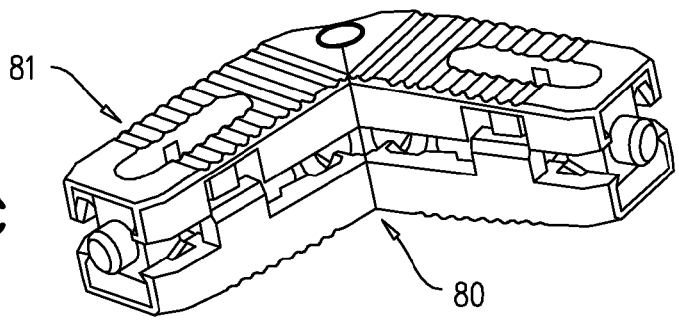

Reference is now made to FIGS. 6A, 6B and 6C, which illustrate a force transmission mechanism 80, constructed and operative in accordance with another embodiment of the invention. Force transmission mechanism 80 can be used in conjunction with any of the wedge or jack expansion mechanisms of the invention.

Force transmission mechanism 80 includes a torque shaft 82 that passes through linking elements 81. Each linking element 81 has upper and lower plates 81A and 81B. Adjacent torque shafts 82 are connected by meshing worm gear mechanisms 84. Such torque shafts can be removable.

Other force transmission mechanisms or elements include, without limitation, chains, cables, flexible shafts, springs, timing belts, bands and wires, laser cut tubes and others.

The scope of the present invention includes both combinations and subcombinations of the features described hereinabove as well as modifications and variations thereof which would occur to a person of skill in the art upon reading the foregoing description and which are not in the prior art.

What is claimed is:

1. An expandable bone device comprising:
   a plurality of linking elements pivotally connected to one another about a hinge, each of said linking elements comprising upper and lower support plates;
   an expansion mechanism operatively connected to said linking elements, and which for each of said linking elements, moves said upper support plate closer or further with respect to said lower support plate, and wherein said upper and lower support plates comprise bending structure such that said upper support plate moves non-parallel and/or non-symmetrically with respect to said lower support plate, and
   a force transmission mechanism for transferring an expansion or turning force to said linking elements, wherein said force transmission mechanism comprises torque shafts that pass through said linking elements and which are connected to each other by a universal joint mechanism or by a worm gear mechanism.

2. The expandable bone device according to claim 1, wherein apertures are formed in said upper and lower support plates, side walls and proximal and distal tips of said linking elements.

3. The expandable bone device according to claim 1, and further comprising a ratchet mechanism comprising a pawl plate that ratchets with teeth formed on a side wall of said linking elements.

4. The expandable bone device according to claim 1, wherein proximal and distal faces of said linking elements are tapered, chamfered or rounded.

5. The expandable bone device according to claim 3, wherein a transverse beam extends between internal faces of side walls of said linking elements.

6. The expandable bone device according to claim 1, wherein said expansion mechanism comprises a wedge mechanism.

7. The expandable bone device according to claim 6, wherein said wedge mechanism comprises a wedge head on an end of a threaded shaft, said wedge head being wedged between upper and lower pivot members.

8. The expandable bone device according to claim 1, wherein said upper support plate is also adapted to move in parallel with respect to said lower support plate.

9. The expandable bone device according to claim 1, wherein at least one of said upper and lower support plates comprises additional attachment structure for attachment as a stand-alone device.

* * * * *